United States Patent [19]

Jeong

[11] Patent Number: 5,654,866
[45] Date of Patent: Aug. 5, 1997

[54] ANION RELEASING APPARATUS FOR VIDEO APPLIANCES

[75] Inventor: Seok Hwa Jeong, Kyungsangbuk-Do, Rep. of Korea

[73] Assignee: LG Electronics Inc., Seoul, Rep. of Korea

[21] Appl. No.: 528,316

[22] Filed: Sep. 14, 1995

[30] Foreign Application Priority Data

Sep. 15, 1994 [KR] Rep. of Korea ............ U94-23988

[51] Int. Cl.⁶ ............................................. H01T 23/00
[52] U.S. Cl. ............................. 361/225; 361/231
[58] Field of Search ........................ 361/212, 213, 361/214, 229, 230, 231

[56] References Cited

U.S. PATENT DOCUMENTS

| | | | |
|---|---|---|---|
| 3,469,031 | 9/1969 | Setchell | 361/231 |
| 4,370,695 | 1/1983 | Penick | 361/213 |
| 5,574,619 | 11/1996 | Jeong | 361/230 |
| 5,576,923 | 11/1996 | Park | 361/213 |

FOREIGN PATENT DOCUMENTS

| | | | |
|---|---|---|---|
| 148596 | 6/1949 | Australia | 361/231 |
| 156930 | 8/1953 | Australia | 361/231 |
| 2452824 | 5/1976 | Germany | 361/231 |
| 392873 | 5/1933 | United Kingdom | 361/231 |

*Primary Examiner*—Fritz Fleming
*Attorney, Agent, or Firm*—Fish & Richardson P.C.

[57] ABSTRACT

The present invention releases anion out of a main body of an end product, driven by convection caused by heat from heating parts inside the main body. According to this apparatus, anions are released out of the main body by circulating convective air flow caused by heat from heating parts at the lowest part inside the main body. Thus an extra fan and the related circuits are unnecessary.

19 Claims, 2 Drawing Sheets

FIG. 1
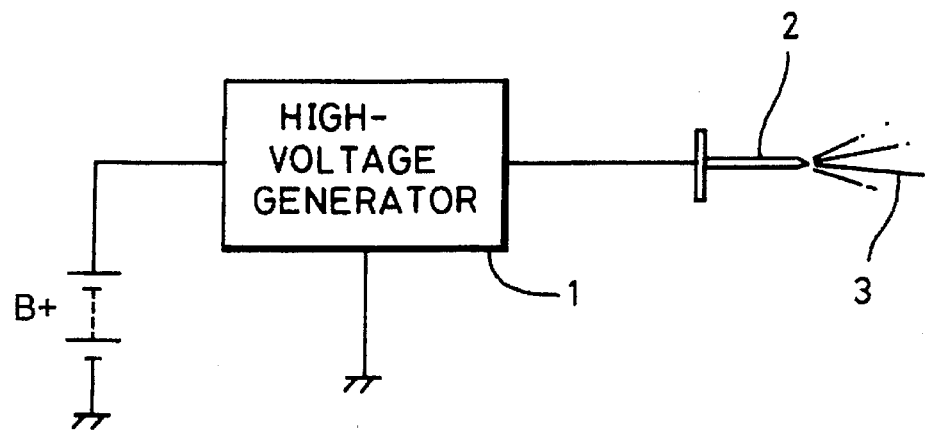
FIG. 2A
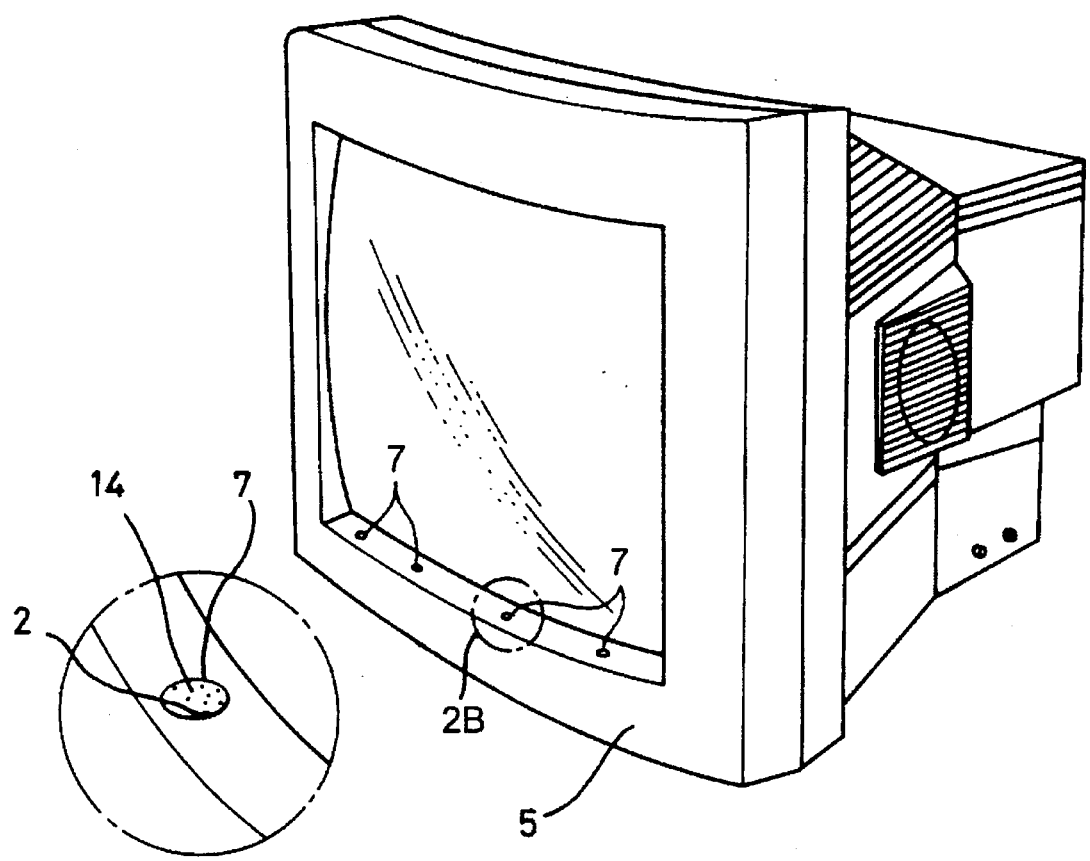
FIG. 2B

ANION RELEASING APPARATUS FOR VIDEO APPLIANCES

BACKGROUND OF THE INVENTION

1. Field of the Invention

The present invention relates to an anion releasing apparatus which is adapted to video appliances. More specifically, this invention relates to an apparatus for releasing anions by releasing anions out of a main body of a product, by driven convective flow caused by heat from heating parts.

2. Description of the Related Art

When using video appliances, such as a television receiver, a computer monitor, an audio-video system, etc., several people usually use them in a limited space. Thus environmental problems arise from their use. The users are exposed to an environment tainted with problems, such as dust, air pollution, cigarette smoke, or the like.

Meanwhile, recent-developed video appliances, having an apparatus for generating anions, create and release anions simultaneously while performing their own functions, so that the environment can be improved.

The conventional video appliances having an apparatus for generating anions adopt an exhaust fan in order to expel anions out of their body. This is the so-called forced blowing method. However, such a method results in other problems. One problem is fan noise which results in another environmental problem; another is the necessity of the additional parts and circuitries for driving the fan, as well as the addition of a fan. The additional parts make it difficult to make the best of the interior space of an end product. This is also contrary to the growing tendency to miniaturize products.

Finally, the cost that is spent on ancillary functions instead of primary functions will be increased. Aside from the increased cost of production of the parts being added, it increases power consumption, design cost, manufacturing cost, etc.

SUMMARY OF THE INVENTION

It is an object of the present invention to provide an anion releasing apparatus for video appliances that releases anions out of a main body of a product, using convection caused by heat radiated from heating parts rather than by an exhaust fan. Therefore, this invention not only achieves the above object but avoids the problems described previously.

To achieve the above object, the present invention provides an anion releasing apparatus in a video appliance including means for generating a high voltage and means for creating anions using a corona discharge with the high voltage from the high voltage generating means, comprising:

means for supporting and fixing said anion creating means, and means for releasing anions created by said anion creating means, using convection caused by heat from heating parts inside the video appliance.

BRIEF DESCRIPTION OF THE DRAWINGS

These and other objects will appear upon reading the following specification and claims and upon considering in connection therewith the corresponding attached drawings.

In the drawings in which a preferred embodiment of the present invention is disclosed:

FIG. 1 shows an anion generation mechanism with an anion generator;

FIG. 2A is a perspective view of a television receiver which adopts an anion releasing apparatus of the present invention;

FIG. 2B is a detailed view of the area within the circle 2B in FIG. 2A;

DETAILED DESCRIPTION OF THE PREFERRED EMBODIMENTS

As known to all, an anion is a general term regarding everything charged with negative electricity, from electron particles to floating matters possessing a diametral size.

There has been several studies on the physiological functions and efficacies of anions. These studies have revealed some efficacies, such as nervous tranquilization, hypnotic alleviation of pain, stirring refreshment, improvement of appetite, relieving nervous fatigue, delaying senescence, etc. In addition to these benefits to a human body, anions quicken the growth of interior plants.

FIG. 1 simply shows an anion generation mechanism of an anion creator adapted to the present invention. As shown, a high-voltage generation circuit 1 generates a high voltage using a DC source (B+). The high voltage is applied to a discharge needle 2 and performs a corona discharge into the air. The air is ionized by such a discharge and a large amount of anions 3 are created.

Figure 3A:
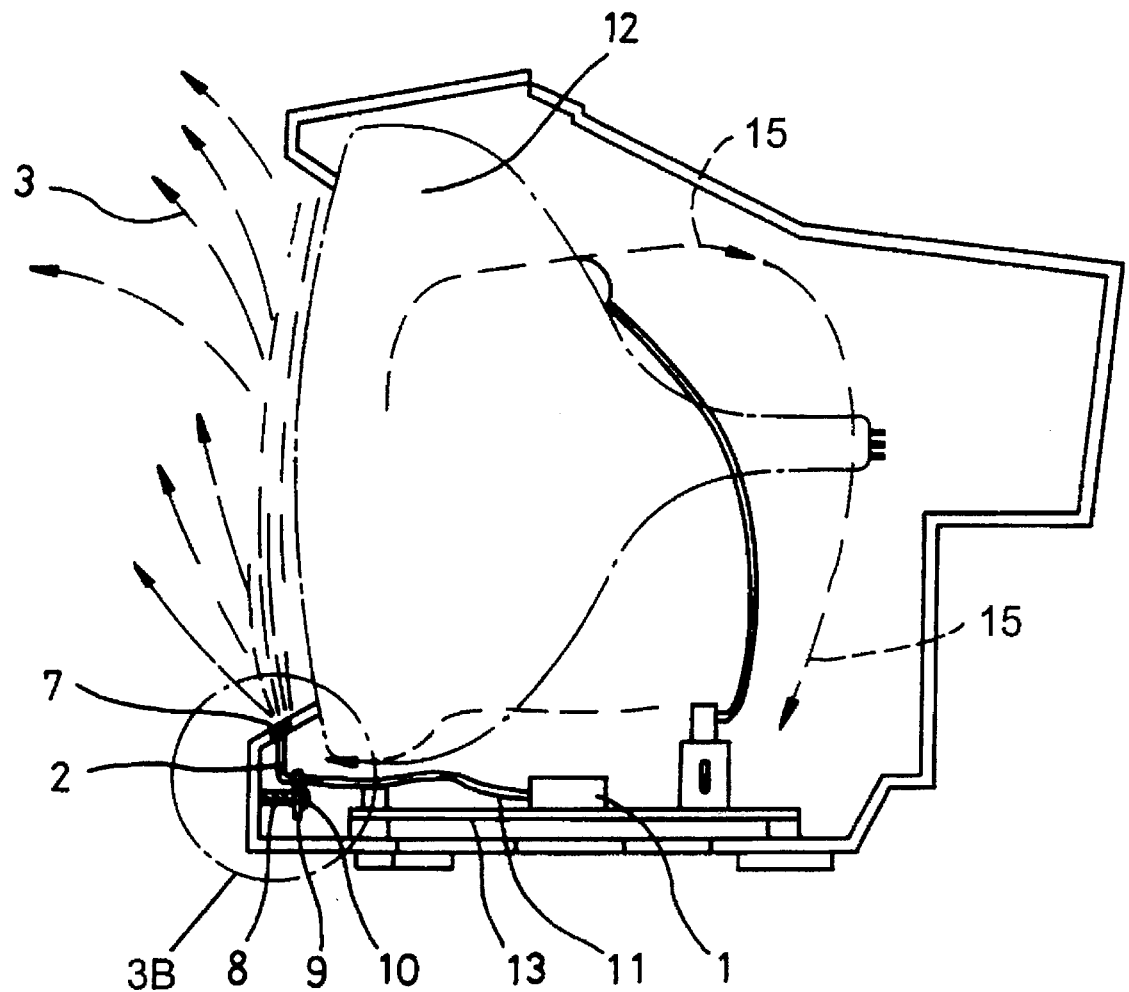
FIG. 3A is a sectional view showing a television receiver which adopts an anion releasing apparatus of the present invention.

A television receiver (TV) which adopts an anion releasing apparatus for video appliances according to the present invention is depicted in FIG. 2A as a perspective view and in FIG. 3A as a sectional view.

With reference to FIGS. 2A and 3A, this apparatus comprises roughly a high-voltage generation circuit 1 which was explained in FIG. 1; a circuit board 13, on which the high-voltage generation circuit 1 is mounted, that is fixed to a proper location below the screen of a cathode ray tube 12; a lowest part inside the TV; a fixing section which is constituted by a set screw 10 for fixing the discharge needle 2, connected to the high-voltage generation circuit 1, to a proper location inside the TV, by a boss 8 formed on an inner surface of a TV enclosure 5 to be combined with the set screw 10, and by a fixing board 9 for fixing the discharge needle 2; and a vent 7 through which the anions created from the discharge needle 2 exit.

Figure 3B:
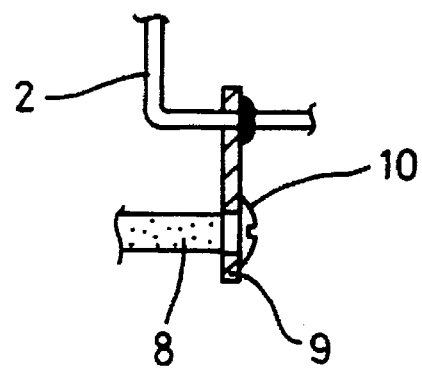
FIG. 3B is a detail of part 3B in FIG. 3A.

FIG. 3B is a detail of the fixing section, which shows the combinational relationship between the discharge needle 2, the boss 8, the fixing board 9, and the set screw 10. To fix the discharge needle 2 with the set screw 10 and boss 8, the discharge needle 2 is held on the fixing board 9. For the fixing board 9 it is preferable to use good insulating materials, so that the insulation between the discharge needle 2 and the set screw 10 can be secured. In this embodiment a printed circuit board of phenol or epoxy substance is used for the fixing board 9, and thus since the discharge needle 2 can soldered on a copper layer of the circuit board, the productivity will increase.

A variety of electric and electronic parts for TV operation is mounted on the circuit board 13. Among the parts, there are heat radiating parts, such as a transformer, a high-power transistor, a power consuming resistor, or a coil, that radiate heat during TV operation. The radiated heat is convected inside the TV and circulates, for example, along the direction of the arrow 15 marked in FIG. 3A.

Since the discharge needle 2 is located at the front lowest part inside the TV, the anions created from the discharge needle 2 is released out of the TV through the vents 7 driven by the circulating air flow within the TV. The released anions spread into a room in the direction of arrows 3 along a surface of a TV screen. Such an operation continues as long as the main system works, i.e., as long as the heating parts radiate heat. Thus anions expelled by convective air flow 15 are gradually diffused in a room.

For lively convection the circuit board on which the heating parts are mounted must be placed at the lowest part inside the TV. To enlarge the amount of anions released, in addition, it is preferable that the discharge needle 2 is located at the point where the velocity of convective flow is maximum.

FIG. 2B shows that anticharge agents 14 are coated on the inner perimeter of the vent 7. These agents prevent the unwanted contaminants, such as dust or a mote, which are ionized together with the anions by the corona discharge, from electrodepositing on the inner perimeter of the vent 7 or on the discharge needle 2. Of course, the agents can prevent the electrodeposition of the anions itself.

As a modified embodiment, the discharge needle 2 can be plurally installed at each of the front corners inside the TV, so that the amount of exiting anions can increase. Of course, it is possible that one high-voltage generator applies a high voltage to several discharge needles.

In effect, when using video appliances, such as a television receiver, a computer monitor, etc., this invention provides a pleasant environment to a user through anions released by convection inside a main body of an end product. Such an effect is obtained even without an extra fan and fan driver. Since there is no fan and the related circuits, the productivity is increased as well as the manufacturing costs is reduced. Environmental debasement due to fan noise is also reduced.

What is claimed is:

1. A video appliance including a high voltage generating circuit positioned inside an enclosure, and a discharge device that creates a corona discharge with a high voltage applied from the high voltage generating circuit to create anions from surrounding air, characterized in that:

the discharge device is positioned at an inner bottom of the enclosure, and the enclosure provides a vent near a predetermined lower part of a display screen of a cathode ray tube, wherein heat radiated by heat radiating elements provided inside the enclosure causes a convective air flow to drive the anions discharged from the discharge device outside through the vent to spread along a surface of the display screen.

2. The video appliance according to claim 1, wherein the discharge device is fixed by a fixing board on a part adjacent to the vent.

3. The video appliance according to claim 1, wherein anticharge agents are coated on an inner perimeter of said vent to prevent electrodeposition of dust, a mote, and said anions.

4. A video appliance including a high-voltage generating circuit positioned inside an enclosure, and a plurality of discharge devices for creating anions to anionize surrounding air by means of a corona discharge with a high voltage applied from the high voltage generating circuit, characterized in that:

the discharge devices are respectively positioned inside of the enclosure; and a plurality of vents are provided near predetermined lower parts of a display screen of a cathode ray tube, wherein heat radiated by heat radiating elements inside the enclosure causes a convective air flow to drive the anions discharged from the discharge devices outside through the vents to spread along a surface of the display screen.

5. A video appliance having an enclosure with an exposed display screen, the video appliance comprising:

a discharge device to create anions from surrounding air within the enclosure; and the enclosure providing a vent structured to release the anions to spread along a surface of the display screen.

6. The video appliance of claim 5, further including an air flow generator to generate an air flow within the enclosure expelling the anions through the vent.

7. The video appliance of claim 6, wherein the air flow generator comprises a heat-radiating element creating a convective air flow within the enclosure to expel the anions through the vent.

8. The video appliance of claim 6, wherein the vent is positioned below the display screen.

9. The video appliance of claim 6, wherein the vent comprises an inner perimeter coated with anticharging agents.

10. The video appliance of claim 6, wherein the discharge device is fixed by a fixing board on a part adjacent to the vent.

11. The video appliance of claim 6, wherein the enclosure provides a plurality of vents structured to discharge the anions to spread along the surface of the display screen.

12. The video appliance of claim 11, wherein the discharge device comprises a plurality of elements, each being positioned adjacent a respective one of the vents.

13. The video appliance of claim 11, wherein the vents are positioned below the display screen.

14. The video appliance of claim 11, wherein the air flow generator comprises heat-radiating elements within the enclosure that create a convective air flow within the enclosure to expel the anions through the vents.

15. The video appliance of claim 11, wherein the vents each comprise an inner perimeter coated with anticharging agents.

16. The video appliance of claim 11, wherein the discharge device is fixed by a fixing board on a part adjacent to the vent.

17. The video appliance of claim 11, wherein vents are positioned at front corners of the enclosure.

18. A video appliance having an enclosure and a display screen, comprising:

a discharge device to create anions from surrounding air within the enclosure;

a heat producing part positioned to heat air within the enclosure to provide a convective flow; and the enclosure providing a vent below the display screen through which the anions are driven out by the convective flow.

19. The video appliance of claim 18, wherein the convective flow drives the anions through the vent to spread along a surface of the display screen.

* * * * *